United States Patent [19]

Douglas et al.

[11] Patent Number: 5,857,983
[45] Date of Patent: Jan. 12, 1999

[54] METHODS AND APPARATUS FOR SAMPLING BODY FLUID

[75] Inventors: Joel S. Douglas, Santa Clara; Jeffrey N. Roe, San Ramon; Ryszard Radwanski; Brent G. Duchon, both of San Jose, all of Calif.

[73] Assignee: Mercury Diagnostics, Inc., Scotts Valley, Calif.

[21] Appl. No.: 858,045

[22] Filed: May 16, 1997

Related U.S. Application Data

[60] Provisional application No. 60/014,133 May 17, 1996 and provisional application No. 60/019,918 Jun. 14, 1996 and provisional application No. 60/023,658 Aug. 1, 1996 and provisional application No. 60/025,340 Sep. 3, 1996 and provisional application No. 60/714,548 Sep. 16, 1996 and provisional application No. 60/710,546 Sep. 17, 1996.

[51] Int. Cl.[6] .................................................... A61B 5/00
[52] U.S. Cl. ......................... 600/538; 600/573; 600/578
[58] Field of Search ................................... 600/573, 576, 600/578, 583; 606/181, 182

[56] References Cited

U.S. PATENT DOCUMENTS

| D. 254,444 | 3/1980 | Levine | D24/2 |
|---|---|---|---|
| 4,360,016 | 11/1982 | Sarrine | 600/576 |
| 4,503,856 | 3/1985 | Cornell et al. | 128/314 |
| 4,517,978 | 5/1985 | Levin et al. | 128/314 |
| 4,622,974 | 11/1986 | Coleman et al. | 128/634 |
| 4,627,445 | 12/1986 | Garcia et al. | 600/583 |
| 4,637,403 | 1/1987 | Garcia et al. | 600/583 |
| 4,648,408 | 3/1987 | Hutcheson et al. | 600/583 |
| 4,653,511 | 3/1987 | Goch | 600/576 |
| 4,653,513 | 3/1987 | Dombrowski | 600/517 |
| 4,658,821 | 4/1987 | Chiodo et al. | 128/314 |
| 4,660,570 | 4/1987 | Dombrowski | 600/578 |
| 4,685,463 | 8/1987 | Williams | 600/549 |
| 4,787,398 | 11/1988 | Garcia et al. | 600/583 |
| 4,790,979 | 12/1988 | Terminiello et al. | 422/56 |

(List continued on next page.)

FOREIGN PATENT DOCUMENTS

| 0453283 | 10/1991 | European Pat. Off. |
|---|---|---|
| 3708031 | 11/1987 | Germany. |
| WO 8504089 | 9/1985 | WIPO. |
| WO 9510223 | 4/1995 | WIPO. |
| WO 9743962 | 11/1997 | WIPO. |

OTHER PUBLICATIONS

Ash, et al., "A Subcutaneous Capillary Filtrate . . . ," ASAIO Journal, 1993, pp. M699–M705.
Ash, et al., "Subcutaneous Capillary Filtrate . . . " ASAIO Journal, 1992, pp. M416–M420.
Critical Reviews in Biochemical Engineering, vol. 18, issue 1, 1990, pp. 29–54.
Brace, et al., "Reevaluation of the needle . . . ," Amer Jrnal of Phy, v 229, 1975, pp. 603–607.
Ginsberg., "An Overview of Minimally . . . ," Clinical Chem, v 38, 1992, pp. 1596–1600.
Janle–Swain, et al. "Use of Capillary . . . ," Trans Am Soc Artif Intern Organs, 1987, pp. 336–340.

(List continued on next page.)

*Primary Examiner*—Max Hindenburg
*Assistant Examiner*—Charles Marmor, II
*Attorney, Agent, or Firm*—Burns, Doane, Swecker & Mathis, LLP

[57] ABSTRACT

Body fluid is sampled by causing a syringe mounted in a housing to be displaced toward a skin surface. The syringe remains in the resulting incision while the surrounding body tissue is stimulated by a stimulator ring to urge body fluid toward the incision. Simultaneously, the syringe is moved relative to the incision to keep the incision open. Such movement of the syringe may comprise reciprocation in the longitudinal or lateral directions, or both. Alternatively, the movement of the syringe may comprise rotation about a longitudinal center line of the syringe, with the pointed end of the syringe being in the shape of one-half of a cone segment. After the body fluid has been pooled, suction is created in a collection tube disposed in communication with the syringe, to draw body fluid inwardly through the syringe.

21 Claims, 4 Drawing Sheets

U.S. PATENT DOCUMENTS

| | | | |
|---|---|---|---|
| 4,805,623 | 2/1989 | Jobsis | 128/633 |
| 4,850,973 | 7/1989 | Jordan et al. | 604/157 |
| 4,858,607 | 8/1989 | Jordan et al. | 128/314 |
| 4,873,993 | 10/1989 | Meserol et al. | 600/573 |
| 4,883,068 | 11/1989 | Dechow | 600/573 |
| 4,895,147 | 1/1990 | Bodicky et al. | 606/182 |
| 4,920,977 | 5/1990 | Haynes | 600/583 |
| 4,924,879 | 5/1990 | O'Brien | 600/583 |
| 4,953,552 | 9/1990 | DeMarzo | 128/635 |
| 4,976,724 | 12/1990 | Nieto et al. | 606/182 |
| 4,994,068 | 2/1991 | Hufnagle | 606/181 |
| 5,002,054 | 3/1991 | Ash et al. | 128/635 |
| 5,014,718 | 5/1991 | Mitchen | 600/584 |
| 5,029,583 | 7/1991 | Meserol et al. | 128/633 |
| 5,054,499 | 10/1991 | Swierczek | 600/583 |
| 5,066,859 | 11/1991 | Mitchen et al. | 600/584 |
| 5,163,442 | 11/1992 | Ono | 600/573 |
| 5,165,418 | 11/1992 | Tankovich | 600/573 |
| 5,201,324 | 4/1993 | Swierczek | 600/583 |
| 5,217,480 | 6/1993 | Haber et al. | 606/182 |
| 5,231,993 | 8/1993 | Haber et al. | 600/683 |
| 5,277,198 | 1/1994 | Kanner et al. | 600/578 |
| 5,282,822 | 2/1994 | Macors et al. | 606/182 |
| 5,318,584 | 6/1994 | Lange et al. | 606/182 |
| 5,320,607 | 6/1994 | Ishibashi | 605/115 |
| 5,368,047 | 11/1994 | Suzuki et al. | 600/578 |
| 5,395,387 | 3/1995 | Burns | 6006/181 |
| 5,402,798 | 4/1995 | Swierczek et al. | 600/583 |
| 5,423,758 | 6/1995 | Shaw | 600/576 |
| 5,569,212 | 10/1996 | Brown | 604/207 |
| 5,582,184 | 12/1996 | Erickson et al. | 600/573 |
| 5,628,309 | 5/1997 | Schrage | 606/182 |
| 5,662,127 | 9/1997 | De Vaughn | 600/578 |
| 5,666,966 | 9/1997 | Horie et al. | 600/583 |
| 5,682,233 | 10/1997 | Brinda | 600/583 |
| 5,746,217 | 5/1998 | Erickson et al. | 606/181 |
| 5,788,652 | 8/1998 | Rahn | 600/576 |

OTHER PUBLICATIONS

Kayashim, et al., "Suction effusion fluid from . . . ," Amer Phys Soc, 1992, pp. H1623–1626.

Korthuis, et al., "Interstitium & Lymphatic Techniques," pp. 326–327.

Turner, et al., "Diabetes Mellitus: Biosensors for . . . ," Biosensors, 1985, pp. 85–115.

METHODS AND APPARATUS FOR SAMPLING BODY FLUID

PRIOR APPLICATIONS

This application claims benefit of provisional applications Ser. No. 08/017,133 filed May 17, 1996; 60/019,918 filed Jun. 14, 1996; 60/023,658 filed Aug. 1, 1996; 60/025,340 filed Sep. 3, 1996; 60/714,548 filed Sep. 16, 1996; and 60/710,456 Sep. 17, 1996; the disclosures of which are incorporated herein by reference.

The present invention is related to inventions disclosed in the following concurrently filed, commonly assigned U.S. applications: Ser. No. 08/857,680, entitled "Body Fluid Sampling Device and Methods of Use" (attorney docket no. 018176-039); Ser. No. 08/857,335, entitled "Disposable Element for Use in a Body Fluid Sampling Device" (attorney docket no. 018186-058); Ser. No. 08/858,042 entitled "Methods and Apparatus for Sampling and Analyzing Body Fluid" (attorney docket no. 018176-059); and Ser. No. 08/585,043, entitled "Methods and Apparatus For Expressing Body Fluid from an Incision" (attorney docket no. 018176-060). The disclosures of those applications are incorporated herein by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5–50 $\mu L$. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes from one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate sites, such as earlobes and limbs, is sometimes practiced to access sites which are less sensitive. These sites are also less likely to provide excellent blood samples and make blood transfer directly to test devices difficult.

Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. No. 4,850,973 and No. 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,368,047, Dombrowski U.S. Pat. No. 4,654,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 and Haber et al. U.S. Pat. No. 5,217,480, disclose combination lancing and blood collection devices which use a diaphragm to create a vacuum over the wound site.

Erickson et al. U.S. Pat. No. 5,582,184 describes a means of collecting and measuring body fluids. This system uses a coaxial syringe and capillary tube disposed within a spacer member. The spacer member limits the depth of syringe penetration, and compresses body tissue around the syringe while the syringe is in the skin, for improving the flow of interstitial fluid to the syringe. A suction device draws body fluid through the syringe and into the capillary tube.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also disclose disposable, single use lancing devices. U.S. Pat. No. 5,421,816; 5,445,611; and 5,458,140 disclose, as a replacement for invasive sampling, the use of ultrasound to act as a pump for expressing interstitial fluid directly through intact (non-lanced) skin. The amount of fluid which can be obtained in that way is very limited, however.

The disclosures of the above patents are incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 µL for one test device and 8 µL for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable sample collection.

SUMMARY OF THE INVENTION

These and other objects are achieved by the present invention, one aspect of which relates to a method of sampling blood comprising the steps of placing a forward end of a housing against a skin surface, advancing a hollow piercing element forwardly to cut an incision through the skin surface, and depressing a ring of body tissue in surrounding relationship to the incision to spread apart sides of the incision while urging body fluid toward and into the incision. Simultaneously, the piercing element is moved within the incision to keep the incision open. A suction is then applied to the piercing element to draw in body fluid from the incision and into a tube communicating with the piercing element.

Another aspect of the invention relates to a sampling device for sampling body fluid. The sampling device comprises a housing, a piercing element carrier mounted in the housing and carrying a hollow piercing element. A tube communicates with the piercing element. A driver mechanism mounted in the housing drives the syringe carrier forwardly to cut an incision in the skin and maintain and end of the piercing element in the incision. A stimulator mechanism disposed on the housing depresses a ring of body tissue in surrounding relationship to the incision to spread apart sides of the incision while urging body fluid toward the incision. A syringe-moving mechanism disposed on the housing moves the end of the piercing element relative to the incision to maintain the incision open while the stimulator mechanism urges body fluid thereto. A suction mechanism disposed on the housing creates a suction in the tube for drawing in body fluid through the piercing element and into the tube.

Still another aspect of the invention relates to a device for obtaining a sampling of a body fluid through the skin comprising a housing member containing a hollow piercing element for piercing the skin. A first spring member disposed in the housing urges the piercing element to protrude from a forward end of the housing sufficient to cut an incision through the skin. A stop member defines a maximum penetration depth of the piercing element. A second spring disposed in the housing partially retracts the piercing element while maintaining a front end of the piercing element in the incision. A tube communicates with a rear end of the piercing element. A suction mechanism creates a suction in the tube for drawing in body fluid through the piercing element.

BRIEF DESCRIPTION OF THE DRAWINGS

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS OF THE INVENTION

Figure 1:
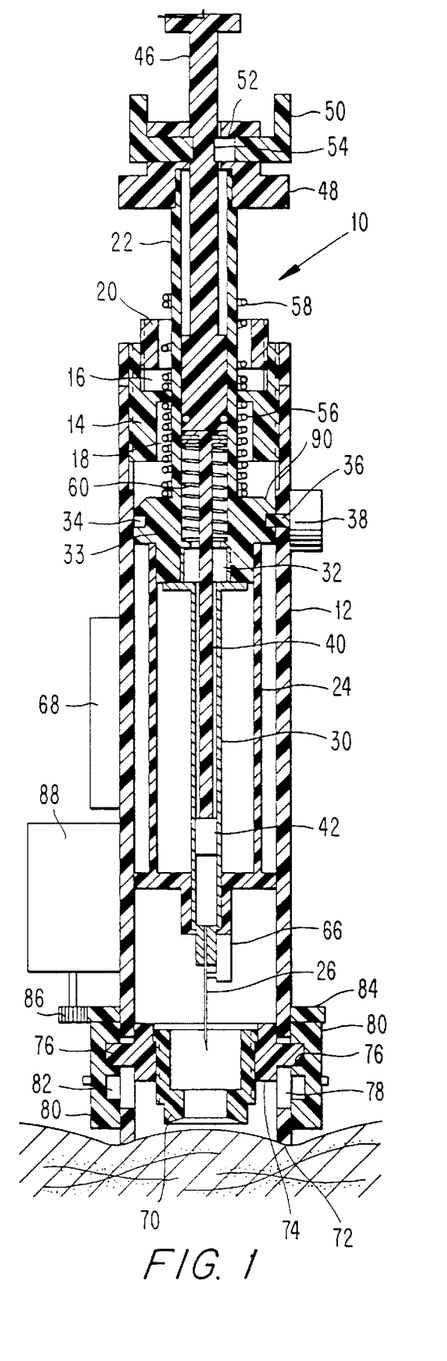
FIG. 1 is a longitudinal sectional view taken through a sampling device according to the present invention, with a syringe thereof in an armed state.
Figure 2:
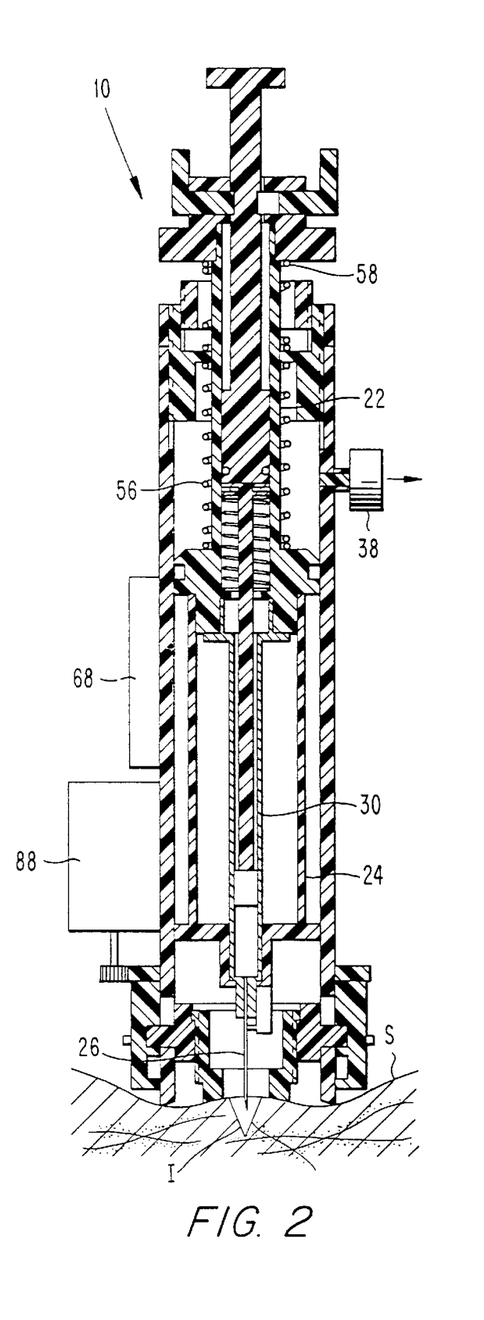
FIG. 2 is a view similar to FIG. 1 after the syringe has been triggered and forms an incision in a skin surface.
Figure 3:
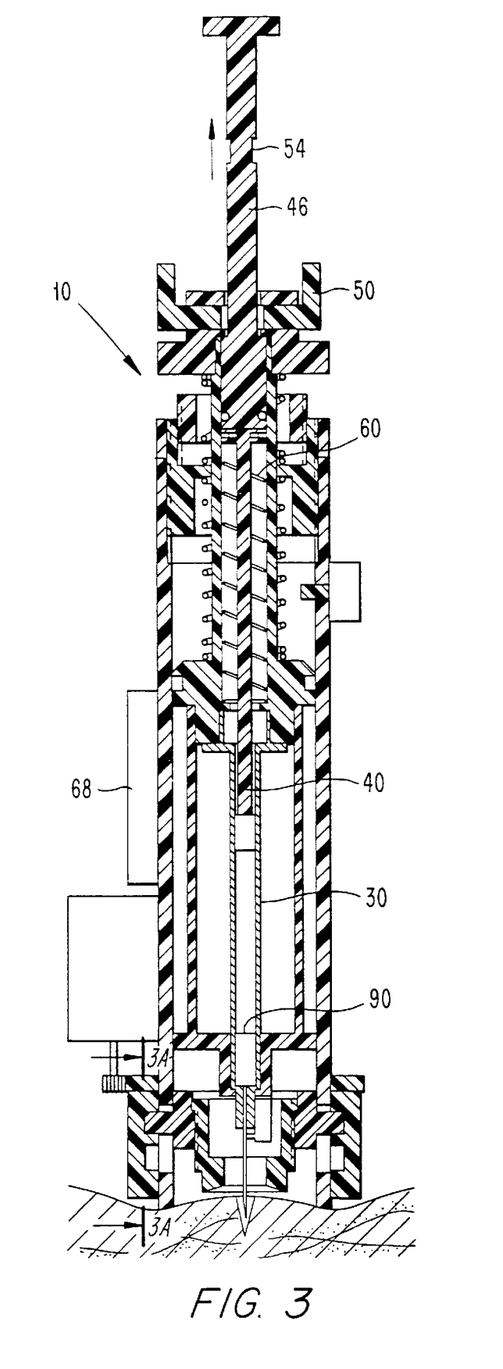
FIGS. 3 is a view similar to FIG. 2 after a suction mechanism has been actuated to draw in body fluid through the syringe.

Depicted in FIGS. 1—3 is a body fluid sampling device 10 comprising an outer cylindrical housing 12. Screwed into an upper end of the housing 12 is a fixing sleeve 14 in which are formed upper and lower recesses 16, 18. The upper recess 16 has an internal screw thread connected to an externally threaded stop ring 20 which can be adjusted to a selected vertical position relative to the housing.

Figure 4:
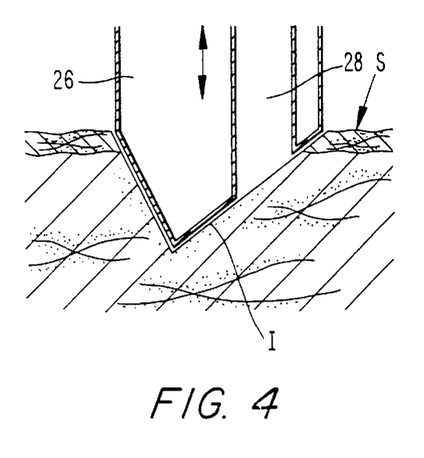
FIG. 4 is a schematic view of a syringe being reciprocated longitudinally within an incision according to the present invention.

Slidably disposed for longitudinal movement within the fixing sleeve 14 is a hollow drive rod 22. Screwed onto a lower end of the drive rod 22 is a syringe carrier 24. Mounted in a lower end of the carrier 24 is a syringe 26 of the type which includes a longitudinal capillary passage 28 (see FIG. 4). That passage is preferably offset laterally with respect to a center axis of the syringe. In lieu of a syringe, any suitable type of hollow piercing element can be employed, such as a needle or sharp cannula, for example.

An upper end of the syringe communicates with a sampling tube 30, an upper end of the tube fitting into a lower recess 32 formed in the drive rod 22.

Intermediate its upper and lower ends, the drive rod 22 includes a radial enlargement 33 in which an outwardly open, annular groove 34 is formed that is sized to receive a pin 36 of a first trigger 38.

Slidably mounted within the sampling tube 30 is a plunger 40 having a soft tip 42 that snugly (sealingly) engages an inner surface of the tube 30. An upper end of the plunger 40 is fixed to the lower end of a drawbar 46 which slides within a center bore of the drive rod 22.

Screwed to an upper end of the drive rod 22 is a mounting sleeve 48 in which a second trigger 50 is mounted for lateral sliding movement. Formed in the second trigger 50 is a center hole 52 that is larger than the outer diameter of the drawbar 46. The drawbar 46 has a recess 54 sized to receive respective sides of the hole 52.

A drive spring 56 in the form of a coil compression spring acts between the enlargement 33 and the fixing sleeve 14. Resting on the fixing sleeve 14 is a retraction spring 58 in the form of a coil compression spring. Acting between the enlargement 33 and the top of the plunger 40 is a suction spring 60 in the form of a coil compression spring.

Mounted on the syringe carrier 24 is a piezoelectric transducer 66 which is electrically connected to a battery 68. Piezoelectric transducers are conventional types of vibrators which can be oriented to produce vibrations in any desired direction. A lower end of the piezoelectric transducer 66 is in contact with the syringe for vibrating the syringe, i.e., either vertically (longitudinally), laterally, or elliptically (a combination of vertical and lateral vibrations).

Disposed at a lower end of the housing 12 is a stimulator sleeve 70. That sleeve has an annular lower face 72 of frusto-conical shape, and is screwed into a sleeve carrier 74. Projecting from diametrically opposite positions of the sleeve carrier 74 are pins 76 which are slidably disposed in respective vertical slots 78 formed in the housing 12.

Figure 3A:
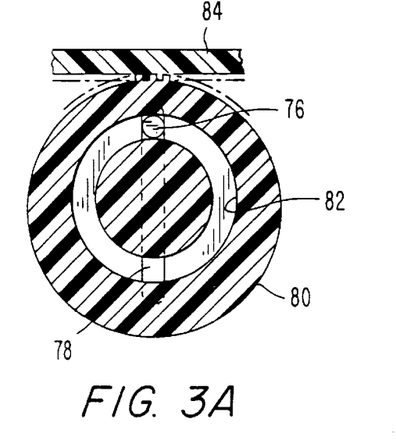
FIG. 3A is a sectional view taken along the line 3A—3A in FIG. 3.

Rotatably mounted on diametrically opposite sides of the housing 12 are a pair of identical drive gears 80 (see also FIG. 3A). Formed in an inner surface of each drive gear 80 is a cam groove 82 in which a respective pin 76 projects. Mounted above the drive gear for rotation about a central longitudinal axis of the housing is a ring gear 84 which is rotated by an output pinion 86 of an electric motor 88. The underside of the ring gear 84 is formed with teeth that mesh with teeth formed around the outer peripheries of the drive gears 80. Therefore, rotation of the pinion gear 86 is transmitted to the drive gears 80 to rotate the drive gears. The accompanying rotation of the eccentric grooves 82 of the drive gears causes the pins 76, and thus the sleeve carrier 74, to reciprocate vertically, along with the stimulator sleeve.

The operation of the sampling device 10 will now be explained. To arm the device, the mounting sleeve 48 is pulled upwardly by a user until a beveled face 90 of the enlargement 33 of the drive rod 22 cams the first trigger laterally outwardly. When the groove 34 of the enlargement becomes aligned with the cammed-out first trigger 38, the first trigger is urged inwardly by a spring (not shown) to insert the pin 36 into the groove 34 for retaining the drive rod 22 in the armed state (FIG. 1). Simultaneously, the drive spring 56 is compressed from a relaxed state, and the syringe carrier 24, together with the syringe 26, is raised. The drawbar 46 is retained by the second trigger 50, with the suction spring 60 disposed in a compressed state.

Figure 5:
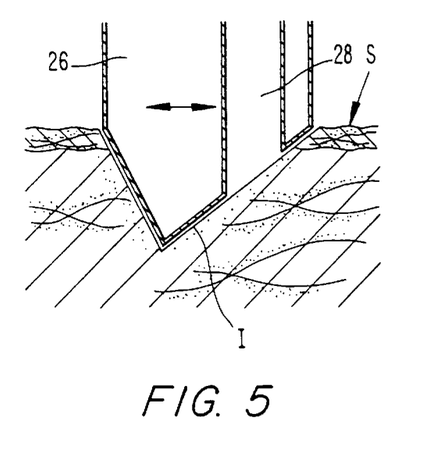
FIG. 5 is a schematic view of a syringe being reciprocated laterally within an incision according to the present invention.
Figure 6:
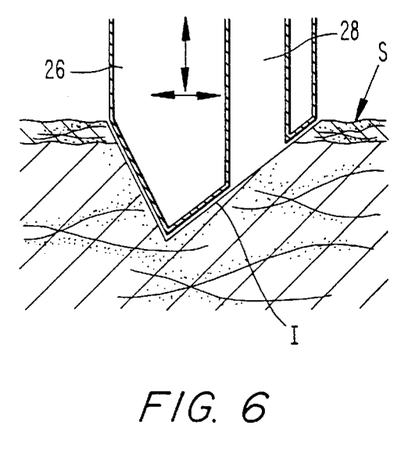
FIG. 6 is a schematic view of a syringe being oscillated in an elliptical direction according to the present invention.

The lower end 72 of the housing 12 is placed against the skin surface S, preferably at a portion of the body having fewer nerve endings than, say the fingertip. A forearm would be a suitable location. The trigger 38 is then pulled out against a spring bias to release the drive rod 22 and the compressed drive spring 56. As a result, the drive rod 22, the syringe carrier 24, and syringe 26 are driven downwardly, so that the syringe cuts an incision I through the skin surface S, as shown in FIG. 2. During downward movement of the drive rod 22, the mounting sleeve 48 engages an upper end of the retraction spring 58 and then abuts the stop ring 20, thereby limiting the incision depth and slightly compressing the retraction spring 58. The retraction spring 58 then moves the drive rod 22 slightly upwardly, but not enough to completely remove the syringe 26 from the incision I. Then, the motor 88 is actuated, either manually, or automatically in response to the firing of the syringe, to vertically reciprocate the stimulator sleeve 70. Consequently, the lower face 72 repeatedly depresses a ring of skin and body tissue which surrounds the incision. Each depression of that ring causes the incision to bulge and the sides of the incision to be spread apart, and urges body fluid such as blood or interstitial fluid toward and outwardly through the incision I, as explained also in commonly assigned concurrently filed U.S. Ser. Nos. 08/857,680 and 08/585,043 (Attorney Docket Nos. 018176-039 and 018176-060). In order to enable the inwardly urged body fluid to pool at the incision (for subsequent sampling), the syringe 26 is vibrated relatively slowly by the piezo-electric transducer 66 to keep the incision open. As noted earlier, the direction of vibration can be determined by the particular orientation of the transducer 66. In one embodiment, the direction of vibration is longitudinal or vertical (FIG. 4); in another embodiment the vibration is lateral (FIG. 5); in another embodiment the vibration is a combination of lateral and vertical, i.e., generally elliptical oscillation (FIG. 6).

It will be appreciated that if the syringe were not moved within the incision, the presence of a stationary syringe within the incision could result in a closing of the incision by collagen in the skin, whereby body fluid could not pool at the incision.

After a short period, sufficient to allow an ample amount of body fluid to pool at the incision, the second trigger 50 is manually actuated to release the drawbar 46, causing the spring 60 to raise the plunger 40 within the tube 30. That produces a suction in the tube 30 below the plunger 40, which draws in a sample 91 of body fluid through the syringe 26 (FIG. 3).

Then, the device can be removed from the skin, and the sample delivered to a suitable test site.

Figure 7:
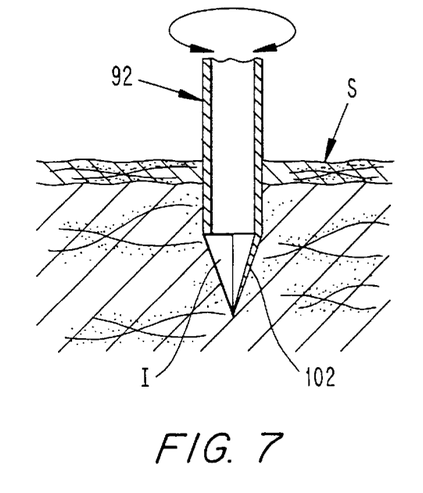
FIG. 7 is a schematic view of a syringe being rotated within an incision according to the present invention.
Figure 8:
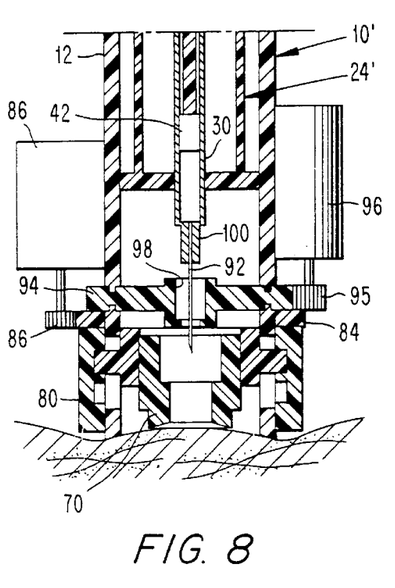
FIG. 8 is a longitudinal sectional view of a lower portion of a modified sampling device according to the present invention, with a syringe disposed in a retracted state.
Figure 9:
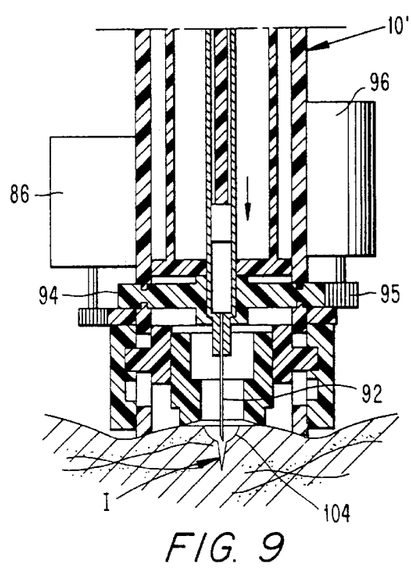
FIG. 9 is a view similar to FIG. 8 after the syringe has been urged forwardly.

As an alternative to the reciprocation of the syringe, the syringe can be rotated about its own center axis while disposed in the incision I. In that regard, a rotatable syringe 92 as shown in FIG. 7 can be utilized in a device 10' shown in FIGS. 8 and 9. That device 10' is similar to that depicted in FIGS. 1–3 with the addition of a rotary gear 94 that is driven by a pinion 95 of a second motor 96. The gear 94 includes an upwardly open recess 98 sized to receive, with a snug fit, a lower end 100 of the tube 30 in which the syringe 92 is disposed. Thus, when the syringe carrier 24' is driven toward the skin, the lower portion 100 of the tube 30 enters the recess 98 to create a frictional engagement between the tube 30 and the gear 94 (see FIG. 9). By then rotating the pinion 95, the gear 94, the tube 30, and the syringe 92 are rotated relative to the carrier 24' about an axis coinciding with a center axis of the syringe 92. The syringe 92 includes a pointed end 102 in the form of one-half of a cone. As the syringe rotates about its own axis, the semiconical segment 102 cuts a conical recess 104 in the incision and keeps the incision open as the stimulator sleeve 70 reciprocates.

Figure 10:
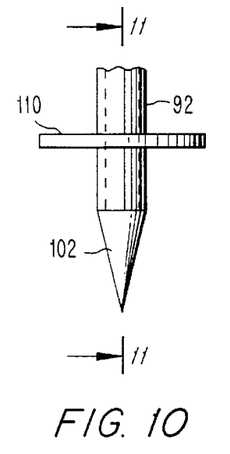
FIG. 10 is a side elevational view of a lower end of a syringe having a stop member fixed thereto according to the present invention.
Figure 11:
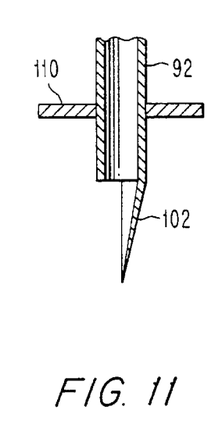
FIG. 11 is a sectional view taken along the line 11—11 in FIG. 10.

Any of the syringes described thus far can be provided with a stop which would replace the stop ring 20. Such a stop 110 is shown in FIGS. 10 and 11 in connection with the syringe 92. The stop 110 comprises a disc fixed to the syringe. When the disc contacts the skin surface, no further entry of the syringe into the skin can occur. The stop ring 20 could also be used to open and close the incision to promote body fluid pooling.

It will be appreciated that the present invention minimizes the pain experienced by a user, because it can be used to provide a sample of body fluid at an area of the body which contains fewer nerve endings than in an area such as the finger tips. By stimulating the body tissue surrounding the incision, while moving the syringe relative to the incision, body fluid is caused to pool in the incision, thereby providing an ample sample to be sucked through the syringe and into a collection tube. Thus, an area of the body less sensitive to pain can be used as a source of body fluid.

Although the stimulator member 70 is disclosed as having a generally annular skin contacting surface, i.e., a surface which is symmetric about the center axis thereof, the member 70 could instead have an elliptical or polygonal end face whereby the ring of body tissue depressed thereby would have a corresponding shape.

Although the present invention has been described in connection with a preferred embodiment thereof, it will be appreciated by those skilled in the art that additions, modifications, substitutions and deletions not specifically described may be made without departing from the spirit and scope of the invention as defined in the appended claims.

What is claimed is:

1. A method of sampling body fluid comprising the steps of:
    A) placing a forward end of a housing against a skin surface;
    B) advancing a hollow piercing element forwardly to cut an incision through the skin surface;
    C) depressing a ring of body tissue in surrounding relationship to the incision to spread apart sides of the incision while urging body fluid toward and into the incision;
    D) moving the piercing element within the incision during step C to keep the incision open; and
    E) applying a suction to the piercing element to draw-in body fluid from the incision and into a tube communicating with the syringe.

2. The method according to claim 1 wherein step C comprises pulsating against the skin a stimulator ring having a front surface surrounding the incision and contacting the skin surface.

3. The method according to claim 2 wherein step D comprises reciprocating the piercing element.

4. The method according to claim 2 wherein step D comprises rotating the piercing element about a center axis of the piercing element.

5. The method according to claim 2 wherein step C further includes reciprocating the stimulator ring in a direction parallel to a center axis of the piercing element.

6. The method according to claim 1, wherein step D comprises reciprocating the piercing element in a direction parallel to a center axis of the piercing element.

7. The method according to claim 1 wherein step D comprises reciprocating the piercing element in a direction perpendicular to a center axis of the piercing element.

8. The method according to claim 1 wherein step D comprises oscillating the piercing element in a generally elliptical direction.

9. The method according to claim 1 wherein step A comprises placing the housing against a skin surface at a location of the body other than a finger tip.

10. A sampling device for sampling body fluid, comprising:
    a housing;
    a carrier mounted in the housing and carrying a hollow piercing element;
    a sample collection tube communicating with the piercing element;
    a driver mechanism mounted in the housing for driving the carrier forwardly to cut an incision in the skin and maintain an end of the piercing element in the incision;
    a stimulator mechanism on the housing for depressing a ring of body tissue in surrounding relationship to the incision to spread apart sides of the incision while urging body fluid toward the incision;
    a moving mechanism on the housing for moving the end of the piercing element relative to the incision to maintain the incision open while the stimulator mechanism urges body fluid thereinto; and
    a suction mechanism disposed on the housing for creating a suction in the tube for drawing-in body fluid through the piercing element and into the tube.

11. The sampling device according to claim 10 wherein the stimulator mechanism comprises a sleeve having a forwardly facing end surface surrounding the piercing element, and a reciprocating mechanism for reciprocating the sleeve in a direction parallel to a center axis of the piercing element.

12. The sampling device according to claim 10 wherein the moving mechanism comprises a mechanism for rotating the piercing element about a center axis thereof.

13. The sampling device according to claim 12 wherein a lower portion of the piercing element is shaped as a half-segment of a cone.

14. The sampling device according to claim 10 wherein the moving mechanism comprises a mechanism for reciprocating the piercing element.

15. The sampling device according to claim 14 wherein the moving mechanism comprises a mechanism for reciprocating the piercing element in a direction parallel to a center axis thereof.

16. The sampling device according to claim 14 wherein the moving mechanism comprises a mechanism for reciprocating the piercing element in a direction perpendicular to a center axis thereof.

17. The sampling device according to claim 14 wherein the moving mechanism comprises a mechanism for oscillating the piercing element in a gene rally elliptical path.

18. The sampling device according to claim 10 further including an adjustable stop mounted on the housing for limiting an insertion depth of the piercing element into the skin.

19. The sampling device according to claim 10 wherein the piercing element has a stop affixed thereto for limiting an insertion depth of the piercing element into the skin.

20. A device for obtaining a sample of body fluid through the skin comprising:

a housing member containing a hollow piercing element for piercing the skin;

a first spring member in the housing for urging the piercing element to protrude from a forward end of the housing sufficient to cut an incision through the skin;

a stop member for defining a maximum penetration depth of the piercing element;

a second spring in the housing for partially retracting the piercing element while maintaining a front end of the piercing element in the incision;

a tube communicating with a rear end of the hollow piercing element; a moving mechanism for moving the piercing element relative to the incision to keep the incision open while body fluid is sampled therefrom, and a suction mechanism in the housing for creating a suction in the tube for drawing-in body fluid through the piercing element.

21. The device according to claim 20 further comprising a stimulator member for depressing a ring of skin and body tissue in surrounding relationship to the incision for spreading apart sides of the incision while urging body fluid toward the incision.

\* \* \* \* \*

UNITED STATES PATENT AND TRADEMARK OFFICE
CERTIFICATE OF CORRECTION

PATENT NO. : 5,857,983
DATED : January 12, 1999
INVENTOR(S) : Douglas et al.

It is certified that error appears in the above-identified patent and that said Letters Patent is hereby corrected as shown below:

On the title page: Item [60]

, in the Related U.S. Application Data section:

change "60/014,133" to --60/017,133--;

change "provisional application No. 60/714,548" to --Application No. 08/714,548--;

change "provisional application No. 60/710,546 Sept. 17, 1996" to --application No. 08/710,456 Sep. 17, 1996--.

Column 1, line 9, after "September 17, 1996" add --; and 08/727,074 filed October 8, 1996--.

Signed and Sealed this

Tenth Day of August, 1999

*Attest:*

Q. TODD DICKINSON

*Attesting Officer*  Acting Commissioner of Patents and Trademarks